United States Patent [19]
Dettling et al.

[11] Patent Number: 5,954,644
[45] Date of Patent: Sep. 21, 1999

[54] METHOD FOR AMBIENT LIGHT SUBTRACTION IN A PHOTOPLETHYSMOGRAPHIC MEASUREMENT INSTRUMENT

[75] Inventors: Allen Dettling, Broomfield, Colo.; Alan Martin, San Jose, Calif.; Kurt Aronow, Lafayette, Colo.

[73] Assignee: Ohmeda Inc., Louisville, Colo.

[21] Appl. No.: 08/823,526

[22] Filed: Mar. 24, 1997

[51] Int. Cl.[6] .................................................. A61B 5/00
[52] U.S. Cl. .................................... 600/322; 600/336
[58] Field of Search ........................... 600/310, 322–328, 600/336, 340, 473, 476; 356/39–41

[56] References Cited

U.S. PATENT DOCUMENTS

| | | | |
|---|---|---|---|
| Re. 33,643 | 7/1991 | Isaacson et al. | 600/336 |
| 3,632,211 | 1/1972 | Sedivy et al. | 356/41 |
| 3,802,776 | 4/1974 | Tchang | 356/41 |
| 3,825,342 | 7/1974 | Lubbers et al. | 356/41 |
| 4,001,667 | 1/1977 | Bober | 323/1 |
| 4,266,544 | 5/1981 | Hamaguri | 600/323 |
| 4,700,708 | 10/1987 | New, Jr. et al. | 600/331 |
| 4,781,195 | 11/1988 | Martin | 600/336 |
| 4,863,265 | 9/1989 | Flower et al. | 600/322 |
| 5,144,951 | 9/1992 | Uematsu et al. | 128/633 |
| 5,149,503 | 9/1992 | Kohno et al. | 422/82.05 |
| 5,152,296 | 10/1992 | Simons | 600/492 |
| 5,385,144 | 1/1995 | Yamanishi et al. | 128/633 |
| 5,503,148 | 4/1996 | Pologe et al. | 600/323 |
| 5,555,882 | 9/1996 | Richardson et al. | 600/336 |
| 5,632,272 | 5/1997 | Diab et al. | 600/323 |

OTHER PUBLICATIONS

"A New Family of Sensors for Pulse Oximetry" by Kastle, Noller, Falk, Bukta, Mayer and Miller Feb. 1997 Hewlett–Packard Journal Article 7.

Sedra et al., "Microelectronic Circuits, 3rd Edition," Saunders College Publishing, pp. 68 & 69, 1991.

*Primary Examiner*—Michael Peffley
*Assistant Examiner*—Bryan K. Yarnell
*Attorney, Agent, or Firm*—Holme Roberts & Owen, LLP

[57] ABSTRACT

An improved photoplethysmographic measurement system is disclosed in which a portion of a time division multiplexed (TDM) signal represents an ambient light level, and other TDM signal portions represent detected levels of two or more centered wavelengths of transmitted light. The ambient and detected light portions of the signal are simultaneously applied to the inputs of an instrumentation amplifier(s) so as to produce a continuous output voltage that is proportional to a difference in voltage between the ambient and detected light portions of a TDM signal. Such an approach provides for ambient light level subtraction with reduced noise and componentry.

26 Claims, 3 Drawing Sheets

METHOD FOR AMBIENT LIGHT SUBTRACTION IN A PHOTOPLETHYSMOGRAPHIC MEASUREMENT INSTRUMENT

FIELD OF THE INVENTION

This invention relates to systems that utilize time division multiplexed (TDM) signals and, more particularly, to an improved photoplethysmographic measurement instrument in which an ambient light component is subtracted from a TDM signal. The invention is particularly apt for implementation using instrumentation amplifiers.

BACKGROUND OF THE INVENTION

In the field of analog data transmission, one efficient data transmission technique is to utilize a TDM signal in which information corresponding with a plurality of sources is transmitted over a single data line. Data corresponding with each source is transmitted over the line in dedicated intervals which are generally regular in duration and sequenced. That is, at one particular point in time, data present on the line corresponds with only one of the sources. If the dedicated interval rate is sufficiently rapid, an apparency of continuous data transmission corresponding with each source is realized at the receiving end of the data line. In this regard, the TDM signal is de-multiplexed at the receiving end so as to separate the data into parallel channels, one corresponding with each source. De-multiplexing is generally performed in a synchronous switching operation.

In some systems, after de-multiplexing, a first series of signal conditioning steps is performed which operate on the parallel channel source data. Thereafter, a second series of steps is performed which, once again, require the signal to be in a TDM form. Re-multiplexing of the parallel channels is necessary to regain the TDM signal format required for the second series of steps. After the second series of signal conditioning steps, the signal is de-multiplexed a second time into parallel channels for completion of analog signal processing. The performance of each multiplexing/de-multiplexing iteration introduces switching noise into the resultant signal(s). As can be appreciated, such noise presents system design considerations and limitations.

Other limitations are also introduced by the performance of multiple de-multiplexing/multiplexing iterations. Specifically, each time either of these operations is performed, the overall parts count in the system is increased. Such an increase may significantly limit the reliability of the system and increase manufacturing costs. Moreover, the associated increase in signal line length resulting from the additional parts, along with their interconnections, may serve to couple still further noise into the system from the ambient environment, thereby reducing system performance.

The noted design considerations/limitations are of particular importance in medical instruments that determine pulse rate and blood oxygen saturation level via measurement of certain blood analytes such as, for example, the concentration (as a percentage of total hemoglobin) of oxyhemoglobin ($O_2Hb$), deoxyhemoglobin (RHb), carboxyhemoglobin (COHb) and methemoglobin (MetHb) of a patient. Such photoplethysmographic measurement instruments are configured to emit light of at least two different, predetermined wavelengths through a selected portion of a patient's anatomy (e.g., a finger tip). The analytes to be identified within the patient's blood must each have unique light absorbance characteristics for at least two of the emitted wavelengths. By measuring changes in intensity of the transmitted (the light exiting an absorber is referred to as transmitted) light from the patient's finger (or other suitable area of anatomy) at these wavelengths, each analyte may be determined. Thereafter, characteristics such as blood oxygen saturation may be determined based on these analytes. Other characteristics such as pulse rate may be determined based on certain components of the transmitted light signal which passes through the patient's anatomy. Specifically, the transmitted light includes a large DC component and a smaller AC or pulsatile component. By using the pulsatile component, the patient's pulse rate may be determined, since fluctuations in the pulsatile component are a function of arterioles pulsating with the patient's heart rate.

In one photoplethysmographic measurement system known as a pulse oximeter, at least two wavelengths of light may be emitted during dedicated, alternating intervals. The transmitted light from the selected body portion is detected by a light-sensitive element (e.g., a photodiode). The light-sensitive element then outputs a TDM signal that includes portions corresponding with each wavelength of the transmitted light. As will be appreciated, the photodiode is also sensitive to light which is present in the ambient environment. Consequently, the TDM output signal can include a corresponding ambient light component. Such component must be removed from the TDM signal for proper processing. For this purpose, at least one interval within a TDM signal is typically dedicated to measuring a component corresponding with only the detected ambient light.

For example in one known pulse oximeter, each emitted light level is immediately preceded by an ambient light interval which may also be referred to as a "dark time" interval. The system first de-multiplexes the TDM signal into parallel channels. Signal processing then proceeds wherein a first series of steps performs preliminary filtering. Immediately following the first series of steps, the parallel channels are re-multiplexed. Next, a second series of steps is performed in which the re-multiplexed signal facilitates subtraction of the dark time signal from the signal corresponding with each emitted light interval in a manner known in the art. Such subtraction process relies on a dark time interval immediately preceding each and every emitted light interval in a TDM format. Following the second series of steps, in which ambient light subtraction is accomplished, the TDM signal is de-multiplexed a second time into parallel channels prior to the completion of signal processing. Such multiple de-multiplexing/multiplexing raises the very noise introduction and cost concerns noted above.

SUMMARY OF THE INVENTION

Accordingly, primary objectives of the present invention are to provide an improved photoplethysmographic measurement system wherein ambient light subtraction from a TDM signal is achieved with reduced noise and/or reduced componentry.

In order to achieve such objectives, a system is provided having at least one TDM signal that includes at least a first identifiable portion that corresponds with detected light from at least one predetermined, light source plus any ambient light present in the system, and a second identifiable portion that corresponds with only the detected ambient light present in the system. In one aspect of the invention, the system further includes amplification means having first and second inputs and an output. The amplification means is configured to produce an amplified output on its output proportional to a difference between signals present on its first and second inputs. Means are provided for substantially simultaneously applying the first TDM signal portion to the first input and for applying the second TDM signal portion to the second input, at substantially the same time, such that the amplified output produced by the amplification means is proportional to the difference between the first and second signal portions, thereby achieving contemporaneous subtraction of the ambient light component and desired signal amplification. The contemporaneous amplification and ambient light level removal may be advantageously performed using an instrumentation amplifier.

In another aspect of the invention, the system is configured for emitting light through a region of interest at two or more different primary wavelengths in an environment which includes an ambient light level. The system separately detects the ambient light level and transmitted light level for each primary wavelength that has passed through the region of interest, such that the levels of detected ambient light and transmitted light form corresponding portions of a TDM signal. The level of transmitted light detected at each primary wavelength includes the ambient light level. To prepare for removing the ambient light level from such transmitted light levels, demultiplexing means is provided for demultiplexing the TDM signal to provide (i) a first portion signal corresponding to the transmitted light level at the first primary wavelength, (ii) a second signal portion corresponding to the transmitted light level at the second primary wavelength and (iii) an ambient light signal portion corresponding to the detected ambient light level. A first subtraction means then produces a first ambient compensated output corresponding to the first primary wavelength by removing the ambient light level from the first signal portion. Similarly, while second subtraction means, separate from the first subtraction means, produces a second ambient compensated output corresponding to the second primary wavelength by removing the ambient light level from the second signal portion. Such separate first and second subtraction means may, for example, comprise first and second instrumentation amplifiers. A processor means is employed to determine the value of the characteristic(s) of interest within the region of interest based on the first and second ambient compensated outputs.

In a primary embodiment of the invention, a photoplethysmographic measurement system includes means for emitting light through a portion of a patient's anatomy at two or more different, predetermined and centered wavelengths (e.g. by intermittent emission). The transmitted portions of the emitted light for each centered wavelength and the ambient light level are detected so as to form respective ambient and detected light signal portions within the TDM signal. First and second amplification means are provided, each of which includes a first input, a second input and an output for producing an amplified output. The output produced by each amplification means is proportional to a difference between signals present on its first and second inputs multiplied by a predetermined and variable gain. The system is configured to apply the ambient light signal to the first input of each amplification means while, at substantially the same time, applying the transmitted detected light signals to the second input of the first and second amplification means. Consequently, the first amplification means produces a first output that is proportional to the difference between the detected signal corresponding to a first predetermined, centered wavelength and the ambient light level; and the second amplification means produces a second output that is proportional to the difference between the detected signal corresponding to a second predetermined, centered wavelength and the ambient light of interest. The first and second amplification means may advantageously comprise separate first and second instrumentation amplifiers, each having a substantively linear response over a frequency range that accommodates the detected light. The first and second outputs from the amplification means are then processed to determine/output certain characteristics including, but not limited to, a patient's pulse rate and blood oxygen saturation level and/or specific blood analyte information such as, for example, the concentration (as a percentage of total hemoglobin) of oxyhemoglobin ($O_2Hb$), deoxyhemoglobin (RHb), carboxyhemoglobin (COHb) or methemoglobin (MetHb) or to otherwise provide an indication when one of such measures exceeds a predetermined level of interest.

The concentrations of a plurality of the noted analytes of interest may be determined by using at least a common plurality of emitted wavelengths, provided that the analytes exhibit unique absorbance behavior at the emitted light wavelengths. By measuring changes in intensity of the transmitted light, for example, from a finger at the emitted wavelengths and based on the corresponding outputs of the amplification means, the aforementioned analytes are among those which may be determined in processing. Thereafter, characteristics such as blood oxygen saturation may be determined based on these analytes. Other characteristics such as pulse rate may be determined based on certain components of the transmitted light signal which passes through the patient's anatomy. Specifically, the transmitted light includes a large DC component and a smaller AC or pulsatile component. By using the pulsatile component, the patient's pulse rate may be determined, since fluctuations in the pulsatile component are a function of arterioles pulsating with the patient's heart rate.

As will be appreciated, the present invention allows a system to be defined that employs only a single demultiplexing step within the overall system. In such a system, a TDM, such as described above, is demultiplexed into (i) a first signal corresponding to transmitted light at the first primary wavelength, (ii) a second output corresponding to the transmitted light at the second primary wavelength and (iii) an ambient light signal corresponding to the detected ambient light level. Thereafter, first and second ambient compensated outputs can be produced by removing the ambient light level from the first and second signals, respectively, using the ambient light signal. The first and second ambient compensated outputs may then be separately conditioned and combinatively processed to determine one or more of the noted characteristics of interest.

Switching noise can be reduced in the present invention since a TDM signal need only be demultiplexed a single time into individual channels.

Additionally, parts count and complexity can be reduced. Finally, as noted, the invention is particularly apt for implementations using instrumentation amplifiers, thereby further yielding improved system performance and reliability.

BRIEF DESCRIPTION OF THE DRAWINGS

For a more complete understanding of the present invention and further advantages thereof, reference is now made to the following Detailed Description, taken in conjunction with the Drawings, in which.

DETAILED DESCRIPTION OF THE INVENTION

Figure 1:
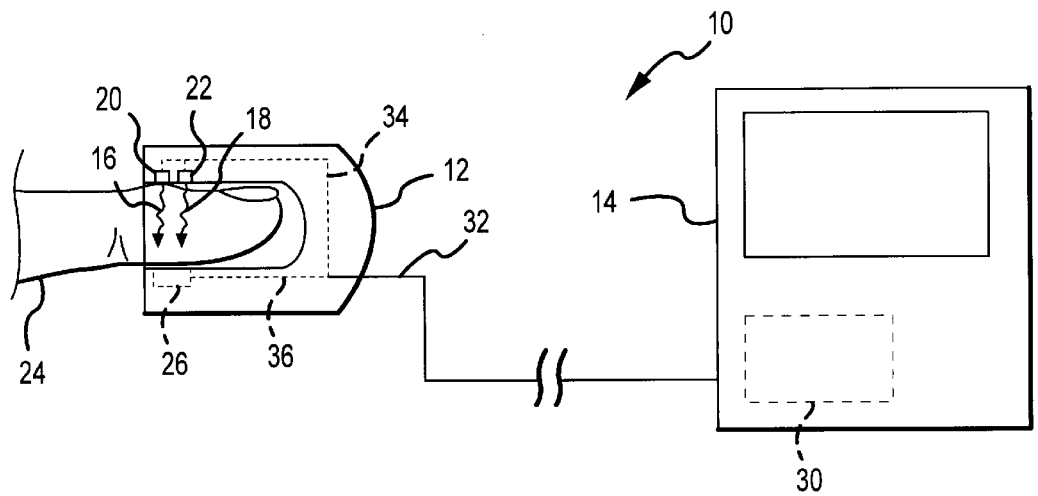
FIG. 1 is a diagrammatic illustration of a photoplethysmographic measurement system implementing the present invention.

FIG. 1 is a diagrammatic illustration of a photoplethysmographic measurement system embodiment, generally indicated by reference numeral 10, constructed in accordance with the present invention. As will be described, the embodiment utilizes a time division multiplexed (TDM) signal in conjunction with an instrumentation-type amplifier. The system is configured to apply specific portions of the TDM signal to the inputs of the instrumentation amplifiers so as to produce continuous output voltages that are proportional to differences in voltage between different portions of the TDM signal.

System 10 includes a sensor probe 12 and a signal conditioning/processing assembly 30 mounted in housing 14. Probe 12 is configured for emitting light 16 centered about a first wavelength and light 18 centered about a second wavelength. Light of the first and second wavelengths is alternately emitted at regular intervals from first and second light sources 20 and 22, respectively, which may, for example, comprise light emitting diodes or laser diodes. One known combination of first and second wavelengths comprises light centered about 660 nm and 940 nm, respectively. It is to be understood, of course, that many other combinations can be employed. Furthermore, it should be appreciated that the present invention can be employed in systems utilizing light of more than two centered, or primary, wavelengths of light.

Continuing to refer to FIG. 1, a portion of the emitted light is transmitted through a portion of a patient's anatomy, such as a finger 24, and is detected by a light-sensitive device. In the described embodiment, a photodiode 26 is utilized. Other areas of the patient's anatomy may also be used provided that the transmitted light suitably passes through such areas. In this regard, the output indications provided by system 10 pertain to arterial blood flow data. More particularly, based upon the absorption of light at the emitted wavelengths certain characteristics may be determined including, but not limited to, a patient's pulse rate and blood oxygen saturation level, including the concentration (as a percentage of total hemoglobin) of oxyhemoglobin ($O_2Hb$), deoxyhemoglobin (RHb), carboxyhemoglobin (COHb) or methemoglobin (MetHb).

Sensor probe 12 is electrically connected to the signal conditioning/processing assembly 30 via multi-conductor cable 32. A first set 34 of conductors within cable 32 carries drive signals to light sources 20 and 22, while a second set 36 of conductors is used to bias photodiode 26 and to carry a TDM signal to the signal conditioning/processing assembly 30.

Figure 2:
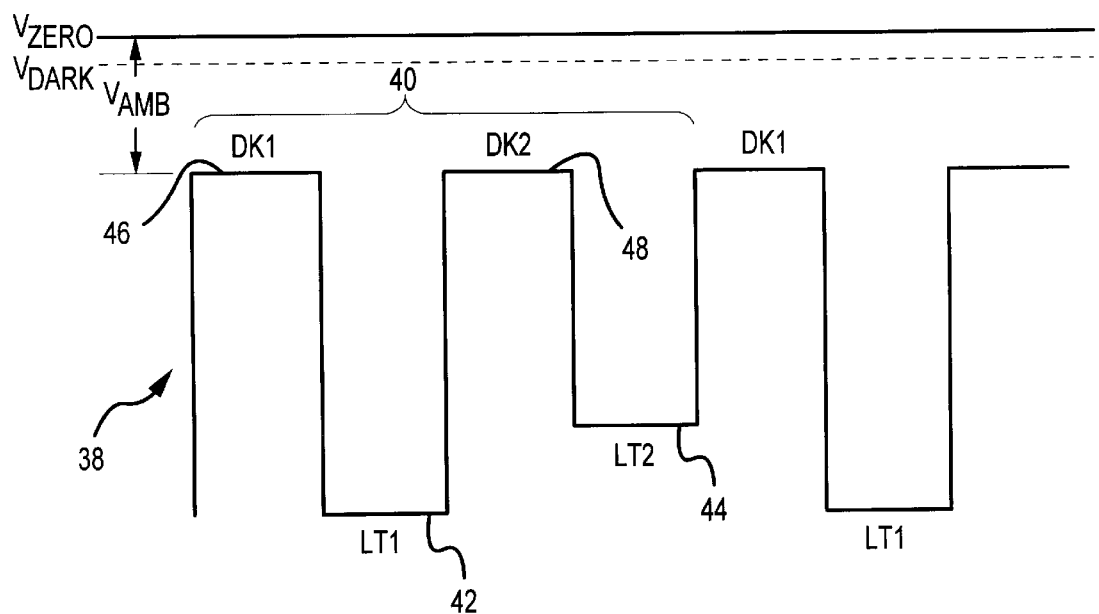
FIG. 2 is a waveform illustrating a TDM signal produced at the preamp output by the system of the present invention.

Referring to FIG. 2 in conjunction with FIG. 1, the TDM signal 38 includes a series of pulse groups 40 output by the photodiode 26 in response to the detection of light passed through finger 24. Each pulse group includes, in this case, a negative going "light 1" (hereinafter "LT1") portion, or interval, and a negative going "light 2" (hereinafter "LT2") portion, or interval, corresponding to the detected levels of light at each of the two transmitted wavelengths. Ambient light is also detected by photodiode 26 together with the detected light corresponding with the light at the first wavelength 16 and light of the second wavelength 18. This ambient light is manifested within the output signal of the photodiode 26 as an offset voltage. That is, the LT1 and LT2 portions each include an offset which results from ambient light that is incident upon the photodiode 26 during the time that the LT1 and LT2 signal portions are generated. In order to facilitate removal of the offset, TDM signal 38 includes a "dark 1"(hereinafter "DK1") portion, or interval, immediately preceding LT1, and a "dark 2"(hereinafter "DK2") interval 48 immediately preceding LT2. The voltage level during each of the DK1 and DK2 intervals represents the ambient light level incident upon photodiode 26 in the absence of transmitted light at the first wavelength 16 or transmitted light at the second wavelength 18.

By way of example and in total darkness, a signal corresponding to $V_{dark}$ is output by the photodiode which may be offset slightly from the zero voltage level $V_{zero}$. The difference in voltage between $V_{zero}$ and DK1, and between $V_{zero}$ and DK2, illustrated as $V_{amb}$, represents the overall ambient light offset present in TDM signal 38. Such an ambient light level may result from any light source including, for example, room lighting or sunlight. As will be appreciated, subtraction of the DK1 and DK2 voltages from the LT1 and LT2 portions, respectively, will result in elimination of both the ambient light data and the photodiode dark current from the signal of interest, i.e., data corresponding with the transmitted light 16 and 18 which has passed through finger 24. It should also be appreciated that ambient light may not produce a D.C. offset as illustrated in FIG. 2. For example, certain common types of lighting induce a time-varying A.C. offset. One such type of lighting is 120 Volt A.C., 60 Hz. powered fluorescent lighting which may produce ambient light pulses at a frequency of 120 Hz. Therefore, circuitry for providing ambient light level subtraction should also be effective in the removal of such time-varying offset signals, as will be described in further detail below.

It is to be understood that TDM signal 38 may be configured in a number of different ways in accordance with the present invention. In the described embodiment, each pulse group 40 includes a dark time interval preceding each light time interval. It is noted that some prior art systems require this signal configuration to perform ambient light subtraction. The present invention also contemplates ambient light subtraction utilizing one dark time interval per each pulse group 40, as will be described further below.

Figure 3:
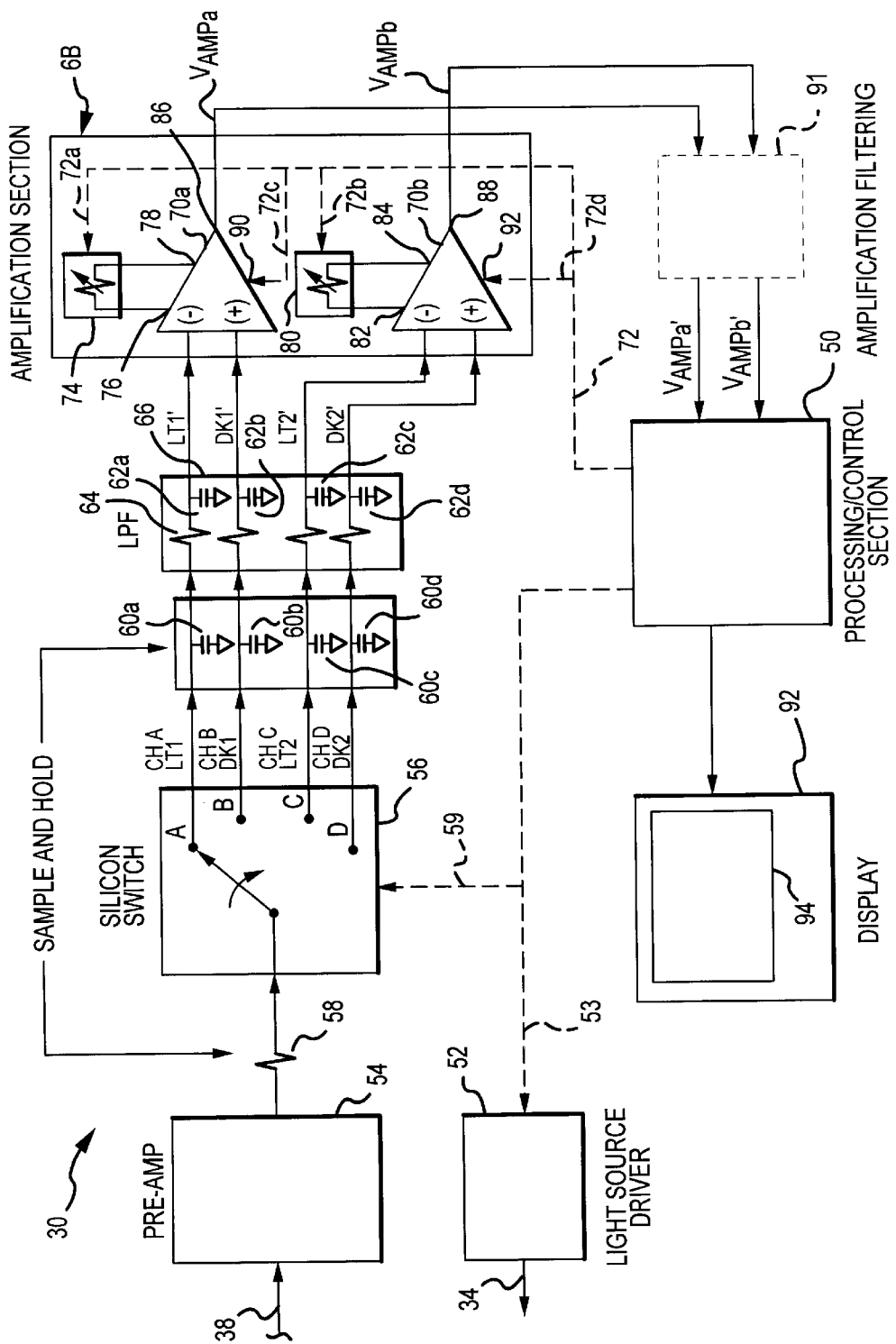
FIG. 3 is a block diagram illustrating the components which make up selected portions of the system of FIG. 1.

Referring to FIGS. 1 through 3, signal conditioning/processing assembly 30 will now be described. A processing/control section 50 is included which provides drive signals to a light source driver section 52 through a control signal line 53. The light source driver section may be configured, for example, to drive LEDs, laser diodes or other such suitable light sources which may become available. The light source driver section 52 provides drive signal waveforms to probe 12 so as to excite sources 20 and 22 to emit light 16 (of the first wavelength) and light 18 (of the second wavelength). In turn, photodiode 26 detects the light passing through the selected body portion to output the TDM signal 38 of FIG. 2.

As shown in FIG. 3, TDM signal 38 is coupled to a preamp section 54 via conductors 36 from probe 12. Preamp 54 converts the relatively small magnitude current of TDM signal 38 to a voltage level more useful for processing. A silicon switch 56 is connected to preamp 54 through resistor 58 (e.g., a 2.1 KW resistor). In the present example, silicon switch 56 comprises a single pole, quadruple throw switch which is controlled by processing/control section 50 by means of control lines 59. Synchronous control of switch 56 is coordinated by processing/control section 50 with drive signals provided to light source driver section 52 such that TDM signal 38 is de-multiplexed. Specifically, silicon switch 56 outputs four data channels A, B, C and D wherein channel A comprises the LT1 signal portion, channel B comprises the DK1 signal portion, channel C comprises the LT2 signal portion and channel D comprises the DK2 signal portion.

Following de-multiplexing, the signal on each channel, A–D, charges one of four holding capacitors 60a–d (e.g., 1.0 µF capacitors). These holding capacitors are configured with resistor 58 to form part of a sample and hold circuit (as well as a low-pass filter) in which an average value of each channel is stored for that cycle.

Thereafter, signals on each of channels A–D are filtered by one of four first order low-pass filters 62a–d. Each filter includes a resistor 64 (e.g., 60.4 KΩ resistors) and a capacitor 66 (e.g., 0.1 µF capacitors). In accordance with the present invention, the sample and hold/low pass circuit comprised of resistor 58, capacitors 60 and silicon switch 56 cooperates with low-pass filters 62 so as to simultaneously and continuously apply signals LT1', DK1', LT2' and DK2' to an amplification section 68. It should be appreciated that the values of resistor 58 and resistors 62, in the low pass filter, are selected along with the values of capacitors 60 and capacitors 62, in the low pass filter, to filter out common, time-varying offset voltages such as those produced by fluorescent lighting to effectively remove the time-varying ambient light signal component. The values of these various passive components may be modified as required by the TDM signal being processed and, in fact, the components may be of different values from one channel to the next for a particular application. For example, the circuitry of FIG. 3 may readily be modified for a TDM signal which includes a single dark time interval per pulse group (not shown). In such a case for a two-wavelength system, channel A may process the LT1 signal, channel B may process the LT2 signal and channel C may process a DK signal, with channel D not being required.

Continuing to refer to FIG. 3, amplification section 68 includes first and second instrumentation amplifiers 70a and 70b. As employed herein, the term "instrumentation amplifier" refers to an amplifier which has an output, $V_{out}=[(V_+ - V_-) G + V_{ref}]$ where $V_+$ and $V_-$ are the inverting and non-inverting inputs, respectively. $V_{ref}$ is a reference voltage which may be set to ground. G is the gain. Typically, the common mode rejection ratio, CMRR, is very high, for example, greater than 100 dB. The instrumentation amplifier may be a single integrated circuit or made up of a group of integrated circuits and/or discrete transistors.

A plurality of control lines 72 connect processing/control section 50 with amplification section 68. Each amplifier 70a, 70b includes an inverting input, indicated by a minus sign, and a non-inverting input, indicated by a plus sign. LT1' and DK1' are applied to the inverting and non-inverting inputs of amplifier 70a, respectively, while L' 2' and DK2' are applied to the inverting and non-inverting inputs of amplifier 70b, respectively. Alternatively, where a single dark time interval is presented within each pulse group, the dark time channel is applied to both of the non-inverting inputs of amplifiers 70a and 70b.

The gain, G, of each amplifier 70a, 70b is adjusted by varying the resistance between a pair of terminals. Specifically, a first variable resistor 74 is connected between terminals 76 and 78 of amplifier 70a, while a second variable resistor 80 is connected between terminals 82 and 84 of amplifier 70b. Variable resistors 74 and 80 are adjusted by processing/control section 50 using control line sets 72a and 72b, respectively. Amplifier 70a includes an output 86 and is configured to output a voltage according to the difference in voltage level between its inverting and non-inverting inputs multiplied by the gain of the amplifier, as determined by the setting of the variable resistor. Amplifier 70b includes an output 88 and is configured in the manner of amplifier 70a. Amplifiers 70a and 70b each include a reference input 90 and 92, respectively. The reference inputs may be grounded but, alternatively, they may be provided with offset voltages $V_{OFFa}$ and $V_{OFFb}$ on control lines 72c and 72d, respectively, which are added to each amplifier's output voltage. Thus, each amplifier outputs a voltage $V_{AMPa}$ or $VAMP_b$, respectively, in accordance with the equations:

$$V_{AMPa}=V_{OFFa}+[GAIN_a \times (LT1-DK1)]; \text{ or}$$

$$V_{AMPb}=V_{OFFb}+[GAIN_b \times (LT2-DK2)]$$

wherein $V_{OFFa}$ and $V_{OFFb}$ are provided from the processing/control section and wherein $GAIN_a$ and $GAIN_b$ are, likewise, determined by the processing/control section and implemented via settings of variable resistors 74 and 80.

$V_{AMPa}$ 86 and $V_{AMPb}$ 88 are provided to an amplification/filtering section 91, then to processing/control section 50.

Following processing, data is provided by processing/control section 50 to a display 92 including a display screen 94 of a suitable configuration including, for example, LCD and CRT types. Information and related warnings are provided in conjunction with or as an alternative to visual display. For example, in the event that the determined value of a monitored characteristic falls above and/or below predetermined threshold values an audio alarm may sound to alert attending medical personnel.

One advantage in the configuration of the circuitry of FIG. 3 relates to control of the gain and offset voltage settings of amplifiers 70 by the processing/control section. Specifically, to achieve a relatively high signal to noise ratio, the gain and offset settings provided by processing/control section 50 should cooperatively center each amplifier's output within the input range of the processing/control measurement system, at the same time, maximizing the swing of the output voltage therebetween without clipping either the top or bottom of the waveform. Processing/control section 50 may accomplish this task by monitoring the $V_{AMPa'}$ and $V_{AMPb'}$ signals received from amplification/filtering section 91, or $V_{AMPa}$ and $V_{AMPb}$, received directly from amplification section 68 using, for example, automatic gain control techniques which have previously been implemented in the art using, for example, control algorithms.

Figure 4:
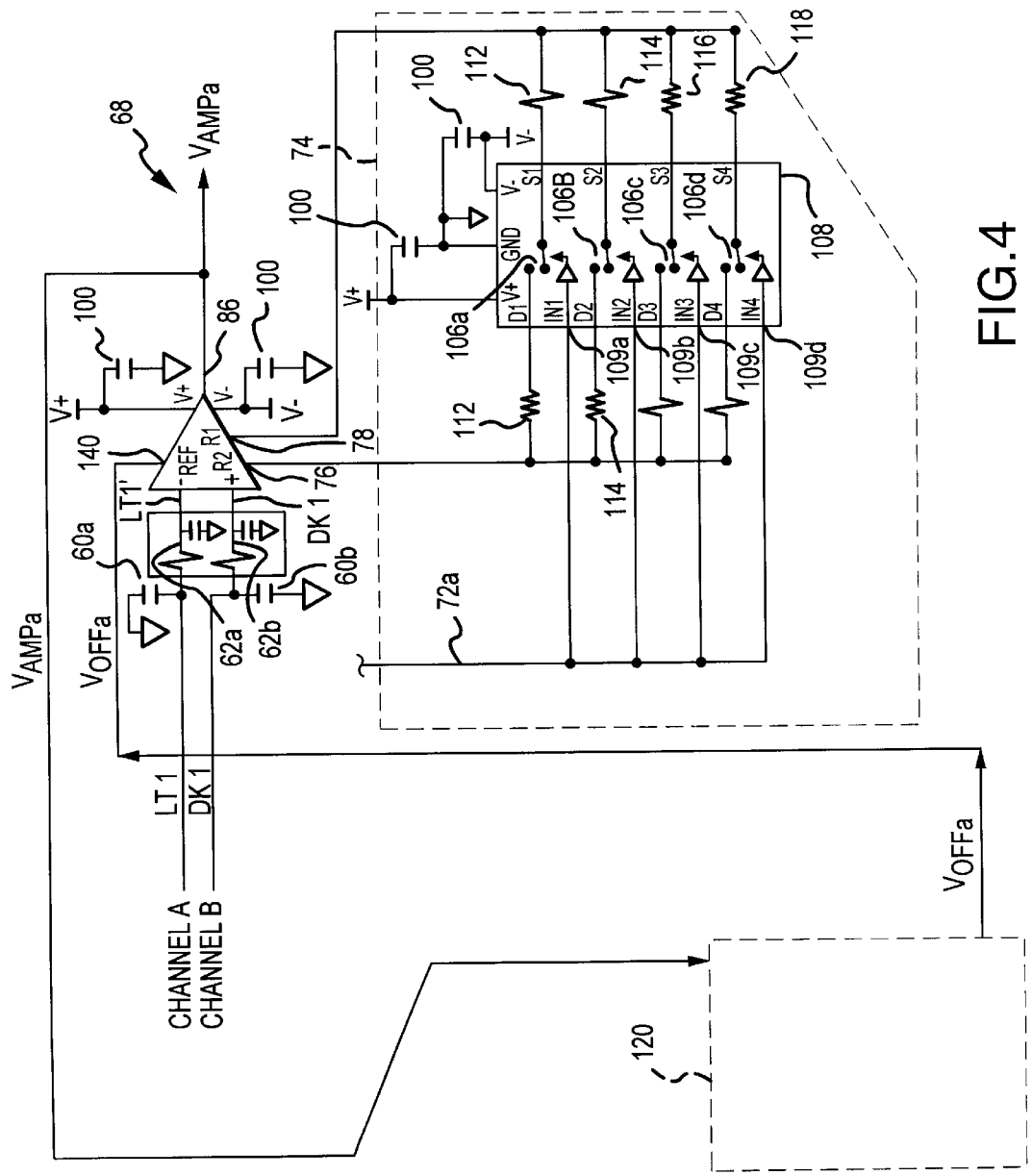
FIG. 4 is a schematic representation of an amplification section used in the system of FIGS. 1 and 3.

FIG. 4 illustrates an amplification section 68. In that all of the instrumentation amplifiers which form part of system 10 are arranged in a directly analogous manner to amplifier 70a, only instrumentation amplifier 70a and its associated circuitry including channels A and B for producing $V_{AMPa}$ will be described in detail. De-multiplexed signals LT1 and DK1 of channels A and B are first applied to capacitors 60a and 60b, respectively, which form the sample and hold circuit in conjunction with resistor 58 (see FIG. 3). Next, the signals are filtered by low-pass filters 62a and 62b to present signals LT' and DK1' to the inverting and non-inverting inputs of amplifier 70a , as previously described. Power supply voltages are applied to amplifier 70a with each of $V_+$ and $V_-$ being filtered by decoupling capacitors 100 (e.g., 0.1 µF capacitors).

Continuing to refer to FIG. 4, variable resistor 74 (indicated within a dashed line) is connected to amplifier 70a, as previously described, at terminals 76 and 78. Control line set 72a from processing/control section 50 provides signals to drive four single pole, single throw switches 106a–d within a readily available solid state switch 108. Each switch 106 is closed by providing a drive voltage to respective ones of a plurality of drive terminals 109a–d. For example, when voltage is connected to drive terminal 109a, switch 106a closes in solid state switch 108. By selectively closing switches 106, predetermined resistance values are connected across terminals 76 and 78. These resistance values are formed by four pairs of resistors 112, 114, 116 and 118 in which each resistor within a pair is of equal resistance (e.g., 24.9 KΩ resistors, 8.25 KΩ resistors, 2.87 KΩ resistors, and 976 Ω resistors, respectively). It is also noted that switches 106 themselves present a series resistance (e.g., 45 ohms). Thus, the load seen by amplifier 70a, appearing across terminals 76 and 78 from each pair of resistors, is balanced with respect to any reactance in switch 108 and is equal to the total resistance of the pair of resistors plus the resistance of the switch itself. In the described embodiment, when switch 106a is closed with switches 106c–d open, the value of the variable resistor 74 is approximately [(24.9 KΩ×2)+45 Ω] or approximately 49.8 KΩ. It should be appreciated that the configuration of variable resistor 74 permits the connection of any combination of these resistance values in parallel across terminals 76 and 78 of the instrumentation amplifier. Therefore, with the four switches shown here, sixteen different combinations are available, each of which produces a predetermined gain when connected with the amplifier. For a typical instruentation amplifier, these gains are calculated using the approximate formula:

$$Gain = 1 + 49.4 \; K/R$$

where R is the resistance applied to terminals 76 and 78 by a particular parallel combination of resistor pairs including the series resistance of switches 106. Table 1 below illustrates the various available gains for the described embodiment.

TABLE 1

|  | SWITCH 106 SETTINGS 0 = OPEN, 1 = CLOSED | | | |
| --- | --- | --- | --- | --- |
| GAIN | SWITCH 106a | SWITCH 106b | SWITCH 106c | SWITCH 106d |
| 1 | 0 | 0 | 0 | 0 |
| 1.991 | 1 | 0 | 0 | 0 |
| 3.986 | 0 | 1 | 0 | 0 |
| 4.977 | 1 | 1 | 0 | 0 |
| 9.539 | 0 | 0 | 1 | 0 |
| 10.53 | 1 | 0 | 1 | 0 |
| 12.53 | 0 | 1 | 1 | 0 |
| 13.52 | 1 | 1 | 1 | 0 |
| 25.74 | 0 | 0 | 0 | 1 |
| 26.73 | 1 | 0 | 0 | 1 |
| 28.72 | 0 | 1 | 0 | 1 |
| 29.71 | 1 | 1 | 0 | 1 |
| 34.28 | 0 | 0 | 1 | 1 |
| 35.27 | 1 | 0 | 1 | 1 |
| 37.26 | 0 | 1 | 1 | 1 |
| 38.25 | 1 | 1 | 1 | 1 |

Still referring to FIG. 4, offset voltage $V_{OFFa}$, is provided to terminal 140 of amplifier 70a from an offset control section 120 which forms part of processing/ control section 50. The offset control section 120 is readily configurable to provide a range of values as offset voltages $V_{OFF}$.

Referring once again to FIGS. 1 and 3, it is readily apparent that in processing of the TDM signal received from probe 12, only one de-multiplexing operation is performed by silicon switch 56. As previously discussed, each multiplexing and/or de-multiplexing step potentially introduces switching noise having significant frequency content. Such noise may result in overall degradation of system performance. Thus, one advantage of the present invention resides in the fact that switching noise is minimized by performing a single de-multiplexing step, as compared with prior art systems which perform more than one de-multiplexing step and more than one multiplexing step.

Another advantage resides in the fact that a decrease in the number of multiplexing and/or de-multiplexing steps is attended by a reduction in the number of parts required in the manufacture of a photoplethysmographic measurement system. This reduction is particularly significant in a two channel system. Reducing the overall parts count of the system results in lower manufacturing costs, improved performance, higher reliability and, possibly, a smaller overall instrument outline. Additionally, since printed circuit boards may be reduced in size whereby to reduce the length of signal paths on the board, noise coupled into the system along the signal path from the ambient environment may also be reduced, resulting in still frrther performance improvements.

Still another advantage is realized by improving signal to noise ratio values through optimizing gain and offset voltage settings. This advantage is implemented through the use of the instrumentation amplifier, as described above. Moreover, prior art systems have generally used gain stages which amplify more than one or, in fact, all of the channels in a system. In these prior art systems, gain settings were basically a compromise in view of all of the data present on the channels being amplified. Such compromise has frequently resulted in increased signal to noise ratios.

It should be understood that a system for performing ambient light subtraction using an instrumentation amplifier in conjunction with a time division multiplexed signal and its associated method may be embodied in many other specific forms without departing from the spirit or scope of the present invention. For example, the present invention is readily adaptable for use in any system which utilizes at least one time division multiplexed signal wherein it is desirable to simultaneously apply different portions of a TDM signal to the inputs of an instrumentation or other such amplifier. Therefore, the described embodiment is to be considered as illustrative and not restrictive, and the invention is not to be limited to the details given herein.

What is claimed is:

1. A photoplethysmographic measurement system for use in determining a value for at least one characteristic derived from a patient's blood using a time division multiplexed signal in an environment including an ambient light level, said system comprising:

means for emitting light through a portion of said patient's anatomy, said light being emitted at two or more different primary wavelengths;

means for detecting said ambient light level and transmitting levels for each said primary wavelength that has passed through said portion of the patient's anatomy such that the detected transmitted levels for each wavelength include the ambient light level and so that the levels of detected ambient light and detected transmitted light form respective ambient and detected light signals within said time division multiplexed signal;

first and second amplification means each of which includes a first input, a second input and an output, each said amplification means being configured for producing a corresponding amplified output that is proportional to a difference between signals present on its first and second inputs multiplied by a corresponding predetermined gain;

means for applying said ambient light signal to said first input of each amplification means while, at the same time, applying said detected light signal to the second input of the first and second amplification means, such that the first amplification means produces a first output that is proportional to the difference between the detected signal corresponding to a first wavelength and the ambient light level and the second amplification means produces a second output that is proportional to the difference between the detected signal corresponding to a second wavelength and the ambient light level, wherein the ambient light level, as indicated by the ambient light signal, is substantially removed from the first and second outputs contemporaneous with the corresponding amplification by said corresponding predetermined gain; and signal processing means for receiving said first and second outputs and for determining said value of said characteristic based upon the first and second outputs.

2. A photoplethysmographic measurement system in accordance with claim 1, further comprising:

means for displaying the value of said characteristic.

3. A photoplethysmographic measurement system in accordance with claim 1, further comprising:

means for providing an alarm if the determined value of said characteristic falls above or below predetermined threshold levels.

4. A photoplethysmographic measurement system in accordance with claim 1, wherein:

said system determines a value for at least one of pulse rate, blood oxygen saturation level, oxyhemoglobin, deoxyhemoglobin, carboxyhemoglobin and methemoglobin.

5. A photoplethysmographic measurement system in accordance with claim 1, each said amplification means further comprising:

an amplifier having a non-inverting input and an inverting input which correspond to said first and second inputs, respectively.

6. A photoplethysmographic measurement system in accordance with claim 5, each said amplification means further comprising:

a series of predetermined resistance values which are selectively connectable with said amplifier for setting the gain of each respective amplification means.

7. A photoplethysmographic measurement system in accordance with claim 6 further comprising:

switching means cooperating with said processing means for connecting the appropriate resistance value to said amplifier so as to set the gain.

8. A photoplethysmographic measurement system in accordance with claim 1 wherein:

said detected light signal includes a first portion generated in response to said first wavelength and a second portion generated in response to said second wavelength, said means for applying the ambient and detected light signals to the amplification means further including a plurality of sample and hold means for continuously providing said ambient light signal to the first input of each of the amplification means and for continuously providing said first portion of the detected light signal to the second input of the first amplification means while continuously providing the second portion of the detected light signal to the second input of the second amplification means such that the output of each amplification means is continuous.

9. A photoplethysmographic measurement system in accordance with claim 8, each said sample and hold means further comprising:

filter means for shaping the respective ambient or detected light signal applied thereto.

10. A photoplethysmographic measurement system in accordance with claim 9, said filter means further comprising:

at least on e low-pass filter.

11. A photoplethysmographic measurement system in accordance with claim 10, said filter means further comprising:

two low-pass filters wherein one low-pass filter includes a roll-off frequency of approximately 7 Hz and another low-pass filter includes a roll-off frequency of approximately 26 Hz.

12. In a photoplethysmographic measurement system, a method of determining a value for at least one characteristic derived from a patient's blood using a time division multiplexed signal in an environment including an ambient light level, said method comprising the steps of:

emitting light through a portion of said patient's anatomy, said light being emitted with two or more different primary wavelengths;

detecting said ambient light level and transmitted levels for each said primary wavelength that has passed through said portion of the patient's anatomy such that the detected transmitted levels for each primary wavelength include the ambient light level and so that the levels of detected ambient light and detected transmitted light form respective ambient and detected light signal portions of said time division multiplexed signal;

providing first and second amplification means each of which includes a first input, a second input and an output, each said amplification means being configured for producing a corresponding amplified output on its output that is proportional to a difference between signals present on its first and second inputs multiplied by a corresponding predetermined gain;

applying said ambient light signal to said first input of each amplification means while, at the same time, applying said detected light signal to the second input of the first and second amplification means, such that the first amplification means produces a first output that is proportional to the difference between the detected signal corresponding to a first primary wavelength and the ambient light level and the second amplification means produces a second output that is proportional to the difference between the detected signal corresponding to a second primary wavelength and the ambient light level, wherein the ambient light level, as indicated by the ambient light signal, is substantially removed from the first and second outputs contemporaneous with the corresponding amplification by said corresponding predetermined gain; and processing said first and second outputs so as to determine said characteristic.

13. The method of claim 12, further comprising the step of:

displaying said characteristic.

14. The method of claim 12, further comprising the step of:

provil an alarm if the predetermined value of said characteristic falls above or below predetermined threshold values.

15. The method of claim 12, and processing step further comprising the step of:

determining a value for at least one of pulse rate, blood oxygen saturation level, oxyhemoglobin, deoxyhemoglobin, carboxyhemoglobin and methemoglobin.

16. The method of claim 12, further comprising the step of:

initially adjusting the gain of each amplification means and, thereafter, readjusting each gain only in response to predetermined physiological changes within said portion of the patient's anatomy or when said light is transmitted through a different portion of the patient's anatomy such that switching noise resulting from gain adjustment of the amplification means is minimized.

17. The method of claim 12 wherein said detected light signal includes a first portion generated in response to said first wavelength and a second portion generated in response to said second wavelength, said step for applying the ambient and detected light signals further comprising the steps of:

continuously providing the ambient light signal to the first input of each amplification means; and continuously providing said first portion of the detected light signal to the second input of the first amplification means while continuously providing the second portion of the detected light signal to the second input of the second amplification means such that the output of each amplification means is continuous.

18. The method of claim 12 further comprising the step of:

de-multiplexing said time division multiplexed signal once within the overall system prior to applying the signal to the amplification means such that multiplex/de-multiplex switching noise is substantially reduced.

19. In a photoplethysmographic measurement system, a method of determining a value of at least one characteristic derived from a patient's blood in an environment including an ambient light level, said method comprising the steps of:

emitting light through a portion of said patient's anatomy, said light being emitted with two or more different primary wavelengths;

detecting said ambient light level and transmitted levels for each said primary wavelength that has passed through said portion of the patient's anatomy such that the detected transmitted levels for each primary wavelength include the ambient light level and so that the levels of detected ambient light and detected transmitted light form separate portions of a time division multiplexed signal;

demultiplexing said time division multiplexed signal into a first signal corresponding to detected transmitted light at said first primary wavelength, a second signal corresponding to said detected transmitted light at said second primary wavelength and an ambient light signal corresponding to said detected ambient light level;

separately conditioning said first signal, said second signal and said ambient light signal to generate a first conditioned output, a second conditioned output and an ambient output, respectively;

directly and substantially contemporaneously using said first conditioned output and said ambient output at a first amplifier to generate a first ambient compensated and amplified output corresponding to said first primary wavelength, said first ambient compensated and amplified output being proportional to a first difference between said first conditioned output and said ambient output multiplied by a first predetermined gain;

directly and substantially contemporaneously using said second conditioned output and said ambient output at a second amplifier to generate a second ambient compensated output corresponding to said second primary wavelength, said ambient compensated and amplified output being proportional to a second difference between said second conditioned output and said ambient output multiplied by a second predetermined gain; and processing said first and second ambient compensated outputs to determine said value of said characteristic.

20. The method of claim 19, wherein:

said step for producing said first ambient compensated output includes the step of substantially contemporaneously amplifying said first conditioned output and said ambient output while removing said ambient light level; and said step for producing said second ambient compensated output includes the step of substantially contemporaneously amplifying said second conditioned output and said ambient output while removing said ambient light level.

21. The method of claim 19, further comprising the step of:

after said processing step, displaying said characteristic.

22. The method of claim 19, further comprising the step of:

after said processing step, producing an alarm if said characteristic falls above or below predetermined threshold levels.

23. A photoplethysmographic measurement system for use in determining a value of at least one characteristic derived from a patient's blood in an environment including an ambient light level, said system comprising:

means for emitting light through a portion of said patient's anatomy, said light being emitted with two or more different primary wavelengths;

means for detecting said ambient light level and transmitted levels for each said primary wavelength that has passed through said portion of the patient's anatomy such that the detected transmitted levels for each wavelength include the ambient light level and so that the levels of detected ambient light and detected transmitted light form separate portion of a time division multiplexed signal;

means for demultiplexing said time division multiplexed signal to provide a first signal corresponding to detected transmitted light at a first primary wavelength, a second signal corresponding to said detected transmitted light at said second primary wavelength and an ambient light signal corresponding to said detected ambient light;

a first amplifier for producing a first ambient compensated output corresponding to said first primary wavelength by removing the ambient light level from said first signal using said ambient light signal, said first amplifier being configured for producing said first ambient compensated output by substantially contemporaneously amplifying said first signal and said ambient light signal by a first predetermined gain while removing said ambient light level;

a second amplifier, separate from said first amplifier, for producing a second ambient compensated output corresponding to said second primary wavelength by removing said ambient light level from said second signal using said ambient light signal, said second amplifier being configured for producing said second ambient compensated output by substantially contemporaneously amplifying said second signal and said ambient light signal by a second predetermined gain while removing said ambient light level; and processing means for determining said value of said characteristic based on said first and second ambient compensated outputs.

24. The photoplethysmographic measurement system of claim 23, wherein:

said first means is configured for producing said first ambient compensated output by substantially contemporaneously amplifying said first signal and said ambient light signal while removing said ambient light level; and said second means is configured for producing said second ambient compensated output by substantially contemporaneously amplifying said second signal and said ambient light signal while removing said ambient light level.

25. The photoplethysmographic measurement system of claim 23, further comprising:

means for displaying said value of said characteristic.

26. The photoplethysmographic measurement system of claim 23, further comprising:

means for providing an alarm if the determined value of said characteristic falls above or below predetermined threshold levels.

* * * * *